United States Patent

Doi et al.

[11] Patent Number: 6,034,285
[45] Date of Patent: *Mar. 7, 2000

[54] PRODUCING METHOD FOR TRIMETHYLOLALKANE

[75] Inventors: Kenji Doi; Takuhiko Jinno; Ayao Moriyama; Michiaki Matsuura, all of Sodegaura, Japan

[73] Assignee: Koei Chemical Company, Limited, Osaka, Japan

[*] Notice: This patent is subject to a terminal disclaimer.

[21] Appl. No.: 09/175,432

[22] Filed: Oct. 20, 1998

[30] Foreign Application Priority Data

Oct. 22, 1997 [JP] Japan .................................. 9-309233

[51] Int. Cl.$^7$ .................................................. C07C 31/18
[52] U.S. Cl. .......................................... 568/853; 568/854
[58] Field of Search .................................... 568/853, 854, 568/913

[56] References Cited

U.S. PATENT DOCUMENTS

| | | | |
|---|---|---|---|
| 4,372,833 | 2/1983 | King, Jr. | 204/157.52 |
| 4,474,959 | 10/1984 | Drury | 544/351 |
| 4,514,578 | 4/1985 | Immel et al. | |
| 4,594,461 | 6/1986 | Merger et al. | |
| 5,149,861 | 9/1992 | Merger | 560/234 |
| 5,334,759 | 8/1994 | Lippert | 562/609 |
| 5,763,690 | 6/1998 | Salek | 568/853 |

FOREIGN PATENT DOCUMENTS

| | | | |
|---|---|---|---|
| 1952738 | 10/1969 | Germany | C07C 31/18 |
| 1952738 | 7/1970 | Germany. | |
| 1553527 | 3/1990 | U.S.S.R. | |
| 9717313 | 5/1997 | WIPO. | |

*Primary Examiner*—Gary Geist
*Assistant Examiner*—Jean F Vollano
*Attorney, Agent, or Firm*—Stevens, Davis, Miller & Mosher, L.L.P.

[57] ABSTRACT

High quality trimethylolalkane can be easily and efficiently produced at a high yield through a reaction between n-alkanal and formaldehyde in the presence of tertiary amine and water, in which a reaction mixture obtained aster the reaction is heated so that a salt of tertiary amine with formic acid produced as a by-product is decomposed into hydrogen and carbon dioxide and/or water and carbon monoxide, and tertiary amine; and the tertiary amine distilled from the reaction mixture is reused in producing trimethylolalkane.

11 Claims, No Drawings

PRODUCING METHOD FOR TRIMETHYLOLALKANE

BACKGROUND OF THE INVENTION

The present invention relates to a method of producing trimethylolalkane by a reaction between n-alkanal and formaldehyde in the presence of tertiary amine and water.

Trimethylolalkane is useful as a raw material for an alkyd resin, a polyurethane resin, a (un)saturated polyester resin, a synthetic lubricating oil, a surfactant, a reactive monomer and the like.

As a known method of producing trimethylolalkane, n-alkanal is reacted with formaldehyde in the presence of a hydroxide of an alkaline metal or an alkali earth metal In this method, alkaline metal formate or alkali earth metal formate is produced as a by-product. Trimethylolalkane is catalytically thermally decomposed by the formate. Accordingly, in conducting distillation, a general isolating and purifying technique for trimethylolalkane, it is necessary to sufficiently separate trimethylolalkane from the alkaline metal formate or the alkali earth metal formate in order to prevent the yield of trimethylolalkane from being lowered by the catalytic thermal decomposition. Thus, the separation is troublesome.

As an improvement of the aforementioned method, a method of producing trimethylolalkane by using tertiary amine and water instead or the hydroxide of an alkaline metal or an alkali earth metal has been proposed (West Germany Patent No. 1952738). In this method using tertiary amine, the formate produced as a by-product is a salt of tertiary amine with formic acid, which does not catalytically thermally decompose trimethylolalkane. Therefore, the thermal decomposition of trimethylolalkane can be suppressed. In this method, the salt of tertiary amine with formic acid is separated from trimethylolalkane by utilizing a difference in the boiling points between the salt and trimethylolalkane.

However, the aforementioned improved method has the following disadvantage. In the separation of a salt of tertiary amine with formic acid from trimethylolalkane by using the difference in the boiling points therebetween, formic acid produced by thermal dissociation of the salt reacts with trimethylolalkane to produce a formate of trimethylolalkane. As a result, the yield of trimethylolalkane is lowered.

SUMMARY OF THE INVENTION

In order to overcome the aforementioned conventional disadvantage, the present inventors have extensively studied a method of producing trimethylolalkane by a reaction between n-alkanal and formaldehyde in the presence of tertiary amine and water. As a result, they have found that lowering yield of trimethylolalkane can be prevented by heating a reaction mixture obtained after the reaction so that a salt of tertiary amine with formic acid included in the reaction mixture can be efficiently decomposed into hydrogen and carbon dioxide and/or water and carbon monoxide, and tertiary amine.

On the basis of this finding, the present invention has been completed.

Furthermore, the tertiary amine produced through the decomposition of a salt of tertiary amine with formic acid can be easily recovered through distillation and can be reused in the production of trimethylolalkane. Thus, another aspect of the invention has been completed.

Specifically, the invention provides:

(1) a method of producing trimethylolalkane which comprises reacting n-alkanal with formaldehyde in the presence of tertiary amine and water, and heating the reaction mixture obtained after the reaction so that a salt of tertiary amine with formic acid produced as a by-product is decomposed into hydrogen and carbon dioxide and/or water and carbon monoxide, and tertiary amine; and (2) a method of producing trimethylolalkane, in which the tertiary amine produced through decomposition of the salt of tertiary amine with formic acid produced as the by-product in the method (1) is recovered through distillation from the reaction mixture and is reused in producing trimethylolalkane.

In this manner, according to the method of producing trimethylolalkane of thin invention, there is no need to separate the salt of tertiary amine with formic acid produced as the by-product from trimethylolalkane after completing the reaction, and production of a formate of trimethylolalkane can be prevented.

DETAILED DESCRIPTION OF THE INVENTION

The production of trimethylolalkane in the present invention through a reaction between n-alkanal and formaldehyde in the presence of tertiary amine and water comprises (1) production of aldol through an aldol condensation reaction between n-alkanal and formaldehyde in the presence of tertiary amine, and (2) production of trimethylolalkane and a salt of tertiary amine with formic acid through a crossed Cannizzaro reaction among aldol, formaldehyde, tertiary amine and water.

Thermal decomposition of the salt of tertiary amine with formic acid produces hydrogen and carbon dioxide and/or water and carbon monoxide, and tertiary amine.

In assuming that triethylamine and n-butanal are used as the tertiary amine and the n-alkanal, respectively, the aldol condensation reaction, the crossed Cannizzaro reaction, the thermal decomposition of the salt of tertiary amine with formic acid in the present method are represented by the following reaction formulas:

(1) Aldol condensation reaction:

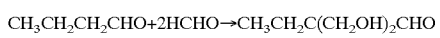

$$CH_3CH_2CH_2CHO+2HCHO \rightarrow CH_3CH_2C(CH_2OH)_2CHO$$

(2) Crossed Cannizzaro reaction:

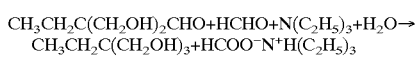

$$CH_3CH_2C(CH_2OH)_2CHO+HCHO+N(C_2H_5)_3+H_2O \rightarrow CH_3CH_2C(CH_2OH)_3+HCOO^-N^+H(C_2H_5)_3$$

(3) Thermal decomposition of the salt of tertiary amine with formic acid:

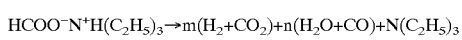

$$HCOO^-N^+H(C_2H_5)_3 \rightarrow m(H_2+CO_2)+n(H_2O+CO)+N(C_2H_5)_3$$

wherein m and n are 0 through 1, and m+n=1.

The aldol condensation reaction and the crossed Cannizzaro reaction of this invention will now be described.

Examples of the n-alkanal used in the present invention include propanal, n-butanal, n-pentanal, 3-methylbutanal, n-hexanal, 3-methylpentanal, n-heptanal, 4-methylhexanal and n-octanal.

An aqueous solution including 5 through 50% by weight formaldehyde is generally used as the formaldehyde in this invention. Preferably, 5 through 50% by weight formalin (namely, a formaldehyde aqueous solution) with a content of methanol of 1% by weight or less is used.

Examples of preferred tertiary amine of this invention include aliphatic tertiary monoamines such as trimethylamine, triethylamine, tri(n-propyl)amine, triisopropylamine, tri(n-butyl)amine, triisobutylamine, diethylmethylamine, dimethylethylamine, dimethyl-n-propylamine, dimethylisopropylamine, dimethyl-n-butylamine and dimethylisobutylamine; aliphatic tertiary diamines such as triethylenediamine, N,N,N',N'-tetramethylethylenediamine and N,N,N',N'-tetramethyl-1,3-propanediamine; and nitrogen heterocyclic tertiary amines such as N-methylmorpholine, N-ethylmorpholine, N-methylpiperidine and N-ethylpiperidine. One or a combination of two or more of these tertiary amines can be used. Particularly preferably, triethylamine is used as the tertiary amine in view of recovering and reusing to the reaction system.

The mole ratio of the formaldehyde to be used is preferably 3 through 4 moles, more preferably 3.2 through 3.6 moles, per 1 mole of the n-alkanal. The mole ratio of the tertiary amine to be used is preferably 1 through 2 moles, more preferably 1.1 through 1.5 moles, per 1 mole of the n-alkanal. When the mole ratio of the formaldehyde exceeds the aforementioned range, the recovery of the tertiary amine becomes difficult. Also, when the mole ratio of the tertiary amine exceeds the aforementioned range, the yield of trimethylolalkane is no longer improving. However, an acid required for neutralization costs more and a longer time is required for the recovery of the tertiary amine.

The amount of water to be used is 200 through 600% by weight, and preferably 250 through 500% by weight on the basis of the total amount of the n-alkanal, the formaldehyde and the tertiary amine.

The aldol condensation reaction is conducted at −5 through 90° C., and preferably, 10 through 60° C. When the temperature is lower than −5° C., the reaction speed is very low, and when the temperature exceeds 90° C., a by-product is easily produced.

The crossed Cannizzaro reaction is conducted at 20 through 90° C., and more preferably, 40 through 80° C. When the temperature is lower than 20° C., the reaction requires a significantly long time, and when the temperature exceeds 90° C., a by-product other than a salt of tertiary amine with formic acid tends to be produced.

In this invention, the aldol condensation reaction and the crossed Cannizzaro reaction are successively proceeded. Therefore, more preferably, the temperature is first set at 10 through 40° C. so as to mainly proceed the aldol condensation reaction, and then set at 40 through 80° C. so as to mainly proceed the crossed Cannizzaro reaction.

After completing the aldol condensation reaction and the crossed Cannizzaro reaction, the resultant reaction mixture is heated, so that the salt of tertiary amine with formic acid as the by-product can be decomposed into hydrogen and carbon dioxide and/or water and carbon monoxide, and tertiary amine.

The reaction mixture can be heated as it is, or heated after removing a part of water therefrom.

When a part of water is removed from the reaction mixture, the content of water in a residue obtained by removing a part of water is at least 20 parts by weight or more, preferably 30 parts by weight or more per 100 parts by weight of the residue. When the content of water in the residue is smaller than this range, formic acid produced through thermal dissociation of the salt of tertiary amine with formic acid reacts with trimethylolalkane, resulting in producing a formate of trimethylolalkane, which may lower the yield of trimethylolalkane.

When the reaction mixture is heated under an increased pressure, the salt of tertiary amine with formic acid can be more easily and more efficiently decomposed.

When no noble metal catalyst is used, the reaction mixture is heated under a pressure of 4.9 Mpa (50 kgf/cm$^2$) or less, and preferably 2.9 through 4.9 MPa (30 through 50 kgf/cm$^2$) at 190 through 300° C., and preferably 200 through 280° C. When the temperature is lower than this range, thermal dissociation of the salt of tertiary amine with formic acid and decomposition of formic acid are difficult to complete. When the temperature exceeds the range, trimethylolalkane can be decomposed.

Also, the decomposition of the salt of tertiary amine with formic acid can be more easily and more efficiently performed by heating the reaction mixture in the presence of a noble metal catalyst.

Examples of the noble metal catalyst include a ruthenium catalyst, a rhodium catalyst, a palladium catalyst, an osmium catalyst, a yttrium catalyst and a platinum catalyst. Among which a palladium catalyst is preferred. Alternatively, a noble metal catalyst obtained by modifying any of these noble metal catalysts with a group 14 element of the periodic table can be used. In particular, a noble metal catalyst modified with lead is preferred. One or a combination of two or more of these noble metal catalysts can be used.

Generally, a noble metal catalyst supported by a carrier, such as carbon, alumina and silica in an amount of 0.5 through 10% by weight is used. The form of the catalyst can be powder, grain or pellet. The suspension method or the fixed bed method is adopted for the heat treatment in the presence of the noble metal catalyst.

The amount of the noble metal catalyst is 1 through 15% by weight per 100% by weight of a formic acid component (HCOOH) in the salt of tertiary amine with formic acid in the reaction mixture after completion of the reactions.

When the decomposition of the malt of tertiary amine with formic acid is conducted in the presence of a noble metal catalyst, the reaction is conducted under atmospheric pressure or an increased pressure of 1.96 MPa (20 kgf/cm$^2$) or less, preferably 0.49 through 1.47 MPa (5 through 15 kgf/cm$^2$) at 50 through 200° C., and preferably 70 through 170° C.

The tertiary amine produced through the decomposition of the salt of tertiary amine with formic acid can be easily distilled from the reaction system and recovered. The tertiary amine thus recovered can be reused for the production of trimethylolalkane of the present invention.

The method of this invention can be carried out by a batch method or a continuous method. Now, a preferred embodiment of the invention adopting the batch method will be described.

While keeping a mixture of formaldehyde (3.2 through 3.6 moles per 1 mole of n-alkanal) and water (250 through 500% by weight based on a total amount of n-alkanal, formaldehyde and tertiary amine) charged in a reactor at 10 through 40° C., n-alkanal and tertiary amine (1 through 2 mole per 1 mole of n-alkanal) are supplied to the reactor over 1 through 3 hours. Subsequently, contents of the reactor is kept at 40 through 60° C. for 1 through 3 hours for completing the aldol condensation reaction, and, then, is kept at 60 through 80° C. for 1 through 2 hours for completing the crossed Cannizzaro reaction.

After completing these reactions, the reaction mixture is treated with a copper oxide catalyst at 60 through 80° C. for 1 through 4 hours, with tertiary amine added if necessary, so that excessive formaldehyde can be changed into methanol and a salt of tertiary amine with formic acid. The amount of the copper oxide catalyst is 0.5 through 5% by weight, and preferably 1 through 3% by weight of the reaction mixture. After the treatment with the copper oxide catalyst, excessive tertiary amine is neutralized with formic acid, and methanol and water are distilled from the reaction mixture under reduced pressure.

When no noble metal catalyst is used, the reaction mixture is heated at 190 through 300° C. under a pressure of 4.9 MPa (50 kgf/cm$^2$) or less, so that the salt of tertiary amine with formic acid can be decomposed into hydrogen and carbon dioxide and/or water and carbon monoxide, and tertiary amine. The obtained tertiary amine is distilled and recovered as an azeotropic mixture with water.

When a noble metal catalyst is used, after adding the noble metal catalyst, the reaction mixture is heated at 50 though 200° C. under atmospheric pressure or an increased pressure of 1.96 MPa (20 kgf/cm$^2$) or less, so that the salt of tertiary amine with formic acid included in the reaction mixture can be decomposed into hydrogen and carbon dioxide and/or water and carbon monoxide, and tertiary amine. The obtained tertiary amine is distilled and recovered as an azeotropic mixture with water.

The recovered mixture of tertiary amine and water is reused for the production of trimethylolalkane.

From the residue from which tertiary amine has been distilled in the aforementioned manner, high quality trimethylolalkane can be easily recovered through distillation or the like.

Now, preferred embodiments of the invention will be described, which do not limit the invention but merely exemplify the invention.

EXAMPLE 1

A reactor with a capacity of 5 liters provided with a thermometer, a reflux condenser, a stirrer and a dropping funnel is charged with 3539.3 g of a 7% aqueous solution of formaldehyde (including 8.25 moles of formaldehyde). While keeping the inner temperature of the reactor at 20° C., 180.3 g (2.50 moles) of n-butanal and 281.1 g (2.78 moles) of triethylamine are added, with stirring, dropwise from separate dropping funnels over 1.5 hours. Subsequently, the temperature is increased to 40° C., and the reaction is allowed to proceed for 1.5 hours. Then, the temperature is increased to 60° C. and the reaction is allowed to proceed for 1 hour, and the temperature is increased again to 80° C. and the reaction is allowed to proceed for another 1 hour. After completion of the reaction, 90 g of a copper oxide catalyst is added, and 49.5 g (0.49 mole) of triethylamine is further added to the reaction mixture. The resultant mixture is stirred for 2 hours at 70° C., thereby treating excessive formaldehyde. The resultant reaction mixture is filtered so as to remove the copper oxide catalyst, and is adjusted to pH 5 by adding 13.0 g of formic acid. From 4063 g of the resultant mixture with pH adjusted, 16.4 g of methanol and 335 g of water are distilled at 60° C. under reduced pressure of 18.66 kPa (140 mmHg). Then, at 80° C. under reduced pressure of 33.32 kPa (250 mmHg), 675 g of water is distilled. The thus obtained residue is heated at 240° C. for 2 hours under a pressure of 3.4 through 3.9 MPa (35 through 40 kgf/cm$^2$). Thus, the salt of triethylamine a with formic acid included in the residue is decomposed into triethylamine, and hydrogen, carbon dioxide, water and carbon monoxide. Water and triethylamine are recovered through distillation, and hydrogen, carbon dioxide and carbon monoxide are removed from the reaction system. In this manner, 328.7 g (3.25 moles) of triethylamine is recovered as a mixture with 2223 g of water. Also, 337.5 g of the residue is obtained, which includes neither formic acid nor a formate of trimethylolpropane. From the thus obtained residue, 285.2 g (2.13 moles) of trimethylolpropane is obtained through distillation under reduced pressure of 0.4 kPa (3 mmHg). The yield on the basis of n-butanal is 85%.

EXAMPLE 2

Triethylamine is separated from the mixture of triethylamine and water recovered in Example 1 at 40° C. By using 140.6 g (1.39 moles) of the separated triethylamine, trimethylolpropane is produced in the same manner as described in example 1 except that the scale of the reaction is halved. As a result, 140.7 g (1.05 moles) of trimethylolpropane is obtained. The yield on the basis of n-butanal is 84%. Also, the residue obtained after distilling triethylamine as an azeotropic mixture with water includes neither formic acid nor the formate of trimethylolpropane.

Comparative Example

From 4388 g of a reaction mixture adjusted to pH 5 obtained in the same manner as described in example 1, 18 g of methanol and 375 g of water are distilled at 60° C. under reduced pressure of 18.66 kPa (140 mmHg). Subsequently, at 80° C. under reduced pressure of 33.32 kPa (250 mmHg), 828 g of water is distilled, and at 50° C. under reduced pressure of 7.33 kPa (55 mmHg), 2301 g of water, 71 g (0.70 mole) of triethylamine and 364 g (2.47 moles) of the salt of triethylamine with formic acid are distilled. From 429 g of the thus obtained residue, which includes 266 g (1.98 moles) of trimethylolpropane (with a yield on the basis of n-butanal of 73%), 110 g of the formate of trimethylolpropane (including 104 g (0.64 mole) of monoester, 6 g (0.03 mole) of diester and a trace amount of triester), and 52 g (0.35 mole) of the salt of triethylamine with formic acid, 150 g of the formate of trimethylolpropane (including 133 g (0.82 mole) of monoester, 8 g (0.04 mole) of diester and a trace amount of triester) and 246 g (1.83 moles) of trimethylolpropane are obtained through distillation under reduced pressure of 0.4 kPa (3 mmHg). The yield on the basis of n-butanal is 68%.

EXAMPLE 3

A reaction mixture adjusted to pH 5 is obtained in the same manner as described in example 1. From 4388.2 g of the thus obtained reaction mixture, 17.7 g of methanol and 350 g of water are distilled under reduced pressure of 18.66 kPa (140 mmHg), and subsequently, 740 g of water is distilled under reduced pressure of 33.32 kPa (250 mmHg). To the this obtained residue, 800 g of 5% palladium/carbon powder (with a 50% moisture content) is added, and the resultant residue is heated at 140° C. under a pressure of 0.98 mPa (10 kgf/cm$^2$) for 2 hours. Thus, the salt of triethylamine with formic acid included in the residue is decomposed, and hydrogen and carbon dioxide are removed from the system. Then, the 5% palladium/carbon powder is filtered. From the thus obtained filtrate, triethylamine and water are distilled as an azeotropic mixture under atmospheric pressure, resulting in recovering a mixture of 355 g (3.51 moles) of triethylazine and 2800 g of water. Subsequently, from 364.5 g of the residue, 304 g (2.27 moles) of trimethylolpropane is obtained through distillation under reduced pressure of 0.4 kPa (3 mmHg) The yield an the basis of n-butanal is 84%. The residue obtained after distilling triethylamine as an azeotropic mixture with water includes neither formic acid nor the formate of trimethylolpropane.

EXAMPLE 4

The mixture of triethylamine and water recovered in example 3 is separated at 40° C., thereby separating 151.8g (1.50 moles) of triethylamine from the mixture. By using the thus separated triethylamine, trimethylolpropane is produced in the same manner as described in example 1 except that the scale of the reaction is halved. As a result, 150 g (1.12 moles) of trimethylolpropane is obtained. The yield on the basis of n-butanal is 83%. The residue obtained by distilling triethylamine as an azeotropic mixture with water includes neither formic acid nor the formate of trimethylolpropane.

EXAMPLE 5

Trimethylolpropane is produced in the same manner as described in example 1 except that 193.1 g (1.49 moles) of N,N,N',N'-tetramethyl-1,3-propanediamine is used instead of triethylamine. As a result, a mixture including 192 g (1.48 moles) of N,N,N,',N'-tetramethyl-1,3-propanediamine and 210 g of water is recovered, and 228 g (1.70 moles) of trimethylolpropane is obtained. The yield on the basis of n-butanal is 63%. The residue obtained after distilling N,N,N',N'-tetramethyl-1,3-propanediamine as a mixture with water includes neither formic acid nor the formate of trimethylolpropane.

EXAMPLE 6

By using the mixture of N,N,N',N'-tetramethyl-1,3-propanediamine and water recovered in example 5, trimethylolpropane is produced in the same manner as described in example 5 except that the scale of the reaction is halved. As a result, 115 g (0.86 mole) of trimethylolpropane is obtained. The yield on the basis of n-butanal is 64%. The residue obtained after distilling N,N,N',N'-tetramethyl-1,3-propanediamine as a mixture with water includes neither formic acid nor the formate of trimethylolpropane.

According to the method of producing trimethylolalkane of this invention, high quality trimethylolalkane can be easily and efficiently produced at a high yield because the salt of tertiary amine with formic acid produced as a by-product is decomposed and the yield of trimethylolalkane is not lowered due to production of the formate of trimethylolalkane. Also advantageously, tertiary amine can be recovered and reused in the production of trimethylolalkane. Thus, the method of producing trimethylolalkane of this invention is a very useful industrial method with remarkable advantages to the conventional techniques.

What is claimed is:

1. A method of producing a trimethylolalkane which comprises (1) a step of reacting an n-alkanal with formaldehyde in the presence of a tertiary amine and water, and (2) a step of heating the reaction mixture obtained after the reaction so that the salt of the tertiary amine with formic acid produced as a by-product is decomposed into at least one of hydrogen, carbon dioxide and the tertiary amine, or into water, carbon monoxide and the tertiary amine.

2. The method of producing a trimethylolalkane according to claim 1, wherein (2) the step of heating the reaction mixture is conducted under an increased pressure.

3. The method of producing a trimethylolalkane according to claim 2, wherein (2) the step of heating the reaction mixture is conducted under an increased pressure of 4.9 MPa or less.

4. The method of producing a trimethylolalkane according to claim 2, wherein (2) the step of heating the reaction mixture is conducted at 190 through 300° C.

5. The method of producing a trimethylolalkane according to claim 2, wherein (2) the step of heating the reaction mixture is conducted after removing a part of water from the reaction mixture.

6. The method of producing a trimethylolalkane according to claim 1, wherein (2) the step of heating the reaction mixture is conducted in the presence of a noble metal catalyst.

7. The method of producing a trimethylolalkane according to claim 6, wherein the noble metal catalyst is a palladium catalyst.

8. The method of producing a trimethylolalkane according to claim 6, wherein (2) the step of heating the reaction mixture is conducted under atmospheric pressure or an increased pressure of 1.96 MPa or less at 50 through 200° C.

9. The method of producing a trimethylolalkane according to claim 1, wherein the tertiary amine is triethylamine.

10. The method of producing a trimethylolalkane according to claim 1, wherein the tertiary amine produced by decomposition of the salt of tertiary amine with formic acid is distilled from the reaction mixture to reuse in a production of trimethylolalkane.

11. The method of producing a trimethylolalkane according to claim 10, wherein the tertiary amine is triethylamine.

* * * * *